(12) United States Patent
Harbige et al.

(10) Patent No.: US 8,114,903 B2
(45) Date of Patent: Feb. 14, 2012

(54) CYTOKINE MODULATORS USING CYCLIC GLYCERIDES OF ESSENTIAL POLYUNSATURATED FATTY ACIDS

(75) Inventors: Laurence S. Harbige, Kent (GB); Michael J. Leach, Kent (GB); Paul Barraclough, Kent (GB); Anthony P Dolan, London (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 12/801,937

(22) Filed: Jul. 2, 2010

(65) Prior Publication Data

US 2010/0297196 A1    Nov. 25, 2010

Related U.S. Application Data

(63) Continuation of application No. 11/885,254, filed as application No. PCT/GB2006/000779 on Mar. 2, 2006, now abandoned.

(30) Foreign Application Priority Data

Mar. 2, 2005   (GB) .................................. 0504362.5

(51) Int. Cl.
*A01N 43/14* (2006.01)
(52) U.S. Cl. ................... 514/452; 424/400; 549/372
(58) Field of Classification Search .............. 424/400; 514/452; 549/372
See application file for complete search history.

(56) References Cited

U.S. PATENT DOCUMENTS

| | | | |
|---|---|---|---|
| 2,077,371 A | 4/1937 | Relneck et at | |
| 2,617,791 A | 11/1952 | Snelling, et at | |
| 3,082,228 A | 3/1963 | Sutherland et al. | |
| 3,158,541 A | 11/1964 | Sutherland et al. | |
| 3,558,656 A | 1/1971 | Pfieffer et al. | |
| 3,658,555 A | 4/1972 | Menz et al. | |
| 3,671,557 A | 6/1972 | Pfeiffer et al. | |

(Continued)

FOREIGN PATENT DOCUMENTS

DE    19503993    8/1996

(Continued)

OTHER PUBLICATIONS

Nakane S et al: "Occurrence of a novel cannabimimetic molecule 2-sciadonoylglycerol (2-eicosa-5',1 1 ',14'-trienoylglycerol)in the umbrella pine *Sciadopitys verticillata* seeds" Biological and Pharmaceutical Bulletin, vol. 23, No. 6, Jun. 2000.*

(Continued)

*Primary Examiner* — Deborah D Carr
(74) *Attorney, Agent, or Firm* — Nixon & Vanderhye

(57) ABSTRACT

A method of treating a patient in need of therapy for a cytokine dysregulation comprising administering to that patient a therapeutically effective dose of a compound of general formula: (I) wherein $R^1$ and $R^2$ together form a group $—(CH_2)_n—CR^4R^5—(CH_2)_m—$ wherein n and m are independently selected integers 0, 1 or 2 and $R^4$ and $R^5$ are independently selected from H, $C_{1-18}$ alkyl, $C_{1-18}$ alkoxy, $C_{1-18}$ n hydroxyalkyl, $C_{2-18}$ alkenyl and $C_{6-18}$ aryl or aralykyl and $R^3$ is the a fatty acyl group of an essential polyunsaturated fatty acid.

(I)

$$R^1—O\phantom{xxx}$$
$$\phantom{xxxxxx}O—R^3$$
$$R^2—O\phantom{xxx}$$

32 Claims, 3 Drawing Sheets

U.S. PATENT DOCUMENTS

| | | | |
|---|---|---|---|
| 3,671,563 A | 6/1972 | Pfeiffer et al. |
| 3,676,472 A | 7/1972 | Zilliken et al. |
| 3,748,348 A | 7/1973 | Sreenivasan, et at |
| 3,855,254 A | 12/1974 | Haighton et al. |
| 3,862,972 A | 1/1975 | Heslinga et al. |
| 3,972,907 A | 8/1976 | Baran et al. |
| 3,993,775 A | 11/1976 | Williams |
| 4,048,202 A | 9/1977 | Beck et al. |
| 4,058,594 A | 11/1977 | Williams |
| 4,181,670 A | 1/1980 | Liang et al |
| 4,607,052 A | 8/1986 | Mendy et al. |
| 4,622,180 A | 11/1986 | Paltauf et al. |
| 4,701,468 A | 10/1987 | Mendy et al. |
| 4,701,469 A | 10/1987 | Mendy et al. |
| 4,826,877 A | 5/1989 | Stewart et al. |
| 4,832,975 A | 5/1989 | Yang |
| 4,851,343 A | 7/1989 | Herbert et al. |
| 4,867,965 A | 9/1989 | Ciaudelli |
| 4,876,107 A | 10/1989 | King et al. |
| 4,938,984 A | 7/1990 | Traitler et al. |
| 5,008,126 A | 4/1991 | Klemann et al. |
| 5,077,312 A | 12/1991 | Shoyab et al. |
| 5,151,291 A | 9/1992 | Tokairin et al. |
| 5,227,403 A | 7/1993 | Seto et al. |
| 5,306,730 A | 4/1994 | Nagai et al. |
| 5,583,159 A | 12/1996 | Horrobin et al. |
| 5,618,955 A | 4/1997 | Mechoulam et al. |
| 5,658,767 A | 8/1997 | Kyle et al |
| 5,661,180 A | 8/1997 | DeMichele et al. |
| 5,663,202 A | 9/1997 | Horrobin et al. |
| 5,668,174 A | 9/1997 | Kawagishi et al. |
| 5,674,901 A | 10/1997 | Cook et al. |
| 5,753,702 A | 5/1998 | Bednar et al. |
| 5,776,913 A | 7/1998 | Ogilvie et al. |
| 5,834,512 A | 11/1998 | Akimoto et al. |
| 5,837,731 A | 11/1998 | Vaddadi |
| 5,869,537 A | 2/1999 | Schreiner et al. |
| 5,914,347 A | 6/1999 | Grinda |
| 5,922,345 A | 7/1999 | Horrobin et al. |
| 5,962,712 A | 10/1999 | DeMichele et al. |
| 5,968,809 A | 10/1999 | Knutzon et al. |
| 5,981,588 A | 11/1999 | Akimoto et al. |
| 5,990,163 A | 11/1999 | Evans et al. |
| 6,015,798 A | 1/2000 | Ogilvie et al. |
| 6,020,376 A | 2/2000 | Pariza et al. |
| 6,051,754 A | 4/2000 | Knutzon et al |
| 6,080,787 A | 6/2000 | Carlson et al. |
| 6,184,251 B1 | 2/2001 | Stordy et al. |
| 6,201,022 B1 | 3/2001 | Mease et al. |
| 6,214,372 B1 | 4/2001 | Jerome et al. |
| 6,262,119 B1 | 7/2001 | Ferrante et al. |
| 6,306,908 B1 | 10/2001 | Carlson et al. |
| 6,331,568 B1 | 12/2001 | Horrobin et al |
| 6,340,485 B1 | 1/2002 | Coupland et al. |
| 6,340,705 B1 | 1/2002 | Obukowicz et al. |
| 6,361,806 B1 | 3/2002 | Allen et al |
| 6,369,252 B1 | 4/2002 | Akoh |
| 6,410,078 B1 | 6/2002 | Cain et al. |
| 6,410,288 B1 | 6/2002 | Knutzon et al. |
| 6,426,100 B2 | 7/2002 | Watkins et al. |
| 6,426,367 B1 | 7/2002 | Das |
| 6,479,070 B1 | 11/2002 | Cain et al. |
| 6,479,544 B1 | 11/2002 | Horrobin |
| 6,495,536 B1 | 12/2002 | Masui et al. |
| 6,528,040 B1 | 3/2003 | Pearson et al. |
| 6,537,750 B1 | 3/2003 | Shorrosh |
| 6,555,579 B2 | 4/2003 | Kritchevsky |
| 6,566,543 B2 | 5/2003 | Mechoulam et al. |
| 6,576,252 B2 | 6/2003 | Schwartz et al. |
| 6,624,195 B2 | 9/2003 | Horrobin |
| 6,630,157 B1 | 10/2003 | Horrobin et al. |
| 6,673,840 B1 | 1/2004 | Oh et al. |
| 6,677,470 B2 | 1/2004 | Saebo et al. |
| 6,689,812 B2 | 2/2004 | Peet et al. |
| 6,841,573 B2 | 1/2005 | Llewellyn |
| 6,852,757 B2 | 2/2005 | Jerome et al. |
| 6,858,416 B2 | 2/2005 | Mukerji et al. |
| 6,864,242 B2 | 3/2005 | Ernest |
| 2001/0047036 A1 | 11/2001 | Vanderhoof et al. |
| 2002/0022658 A1 | 2/2002 | Das |
| 2002/0051964 A1 | 5/2002 | Surai et al. |
| 2002/0065319 A1 | 5/2002 | Horrobin |
| 2002/0072539 A1 | 6/2002 | Mechoulam et al. |
| 2002/0081366 A1 | 6/2002 | Cain et al. |
| 2002/0082436 A1 | 6/2002 | Jerome et al. |
| 2002/0198177 A1 | 12/2002 | Horrobin |
| 2003/0013759 A1 | 1/2003 | Das |
| 2003/0031753 A1 | 2/2003 | Watkins et al. |
| 2003/0032674 A1 | 2/2003 | Hwang ........................ 514/560 |
| 2003/0045460 A1 | 3/2003 | Fogelman et al. |
| 2003/0045578 A1 | 3/2003 | Horrobin |
| 2003/0166723 A1 | 9/2003 | Nakajima et al. |
| 2004/0014810 A1 | 1/2004 | Horrobin et al |
| 2004/0019109 A1 | 1/2004 | Owman et al. |
| 2004/0039058 A1 | 2/2004 | Ursin et al. |
| 2004/0043963 A1 | 3/2004 | Wadstein |
| 2004/0048926 A1 | 3/2004 | Hoffman et al. |
| 2004/0048927 A1 | 3/2004 | Horrobin |
| 2004/0096468 A1 | 5/2004 | Changaris |
| 2004/0102519 A1 | 5/2004 | Llewellyn |
| 2004/0162348 A1 | 8/2004 | Peet et al. |
| 2004/0171688 A1 | 9/2004 | Bar-Tana |
| 2004/0208939 A1 | 10/2004 | Sears et al. |
| 2004/0209953 A1 | 10/2004 | Wai Lee |
| 2004/0220081 A1 | 11/2004 | Kreitz et al. |
| 2004/0229950 A1 | 11/2004 | Vanderhoek |
| 2004/0248763 A1 | 12/2004 | Freeman et al. |
| 2004/0266874 A1 | 12/2004 | Akimoto et al. |
| 2005/0009779 A1 | 1/2005 | Kiliaan et al. |
| 2005/0020679 A1* | 1/2005 | Makriyannis et al. ......... 514/548 |
| 2005/0025744 A1 | 2/2005 | Lane ........................... 424/85.6 |
| 2005/0027004 A1 | 2/2005 | Kyle et al. |
| 2005/0042256 A1 | 2/2005 | Decombaz et al. |
| 2005/0123479 A1 | 6/2005 | Ferrante |
| 2009/0137660 A1 | 5/2009 | Harbige et al. ................ 514/452 |

FOREIGN PATENT DOCUMENTS

| | | |
|---|---|---|
| DE | 100 29 562 | 3/2001 |
| EP | 0 505 812 A | 9/1992 |
| EP | 0 609 078 A | 8/1994 |
| EP | 0490 561 | 3/1996 |
| EP | 0 707 850 | 4/1996 |
| EP | 0 711 503 | 5/1996 |
| EP | 0 766 961 | 4/1997 |
| EP | 0 790 056 | 8/1997 |
| EP | 0 891 773 | 1/1999 |
| EP | 0 679 057 | 8/1999 |
| EP | 0 796 238 | 5/2000 |
| EP | 0 568 608 | 9/2000 |
| EP | 1 077 061 | 2/2001 |
| EP | 1 091 659 | 5/2002 |
| EP | 0 956 011 | 6/2002 |
| EP | 1 035 846 | 7/2002 |
| EP | 0 920 300 | 4/2003 |
| EP | 0 956 013 | 4/2003 |
| EP | 0 800 584 | 5/2003 |
| EP | 1 325 747 A2 | 7/2003 |
| EP | 1 325 747 A3 | 7/2003 |
| EP | 1 342 787 | 9/2003 |
| EP | 1 129 711 | 1/2004 |
| EP | 0 994 705 | 3/2004 |
| EP | 1 292 288 | 9/2004 |
| EP | 1 221 867 | 11/2004 |
| EP | 1506778 | 2/2005 |
| GB | 1 490 603 | 11/1977 |
| GB | 2 409 644 | 7/2005 |
| WO | WO 90/12080 | 10/1990 |
| WO | WO 96/05164 | 2/1996 |
| WO | WO 96/40106 | 12/1996 |
| WO | WO 97/04127 | 2/1997 |
| WO | WO 98/16215 | 4/1998 |
| WO | WO 98/44917 | 10/1998 |
| WO | WO 98/46763 | 10/1998 |
| WO | WO 98/46764 | 10/1998 |
| WO | WO 98/46765 | 10/1998 |
| WO | WO 99/51560 A1 | 10/1999 |
| WO | WO 99/64389 A1 | 12/1999 |

| WO | WO 00/09476 | 2/2000 |
| WO | WO 00/12720 | 3/2000 |
| WO | WO 00/21524 | 4/2000 |
| WO | WO 00/34791 | 6/2000 |
| WO | WO 00/40705 | 7/2000 |
| WO | WO 00/44360 | 8/2000 |
| WO | WO 00/53637 | 9/2000 |
| WO | WO 00/74669 | 12/2000 |
| WO | WO 01/10989 | 2/2001 |
| WO | WO 01/13733 | 3/2001 |
| WO | WO 01/17366 | 3/2001 |
| WO | WO 01/17524 | 3/2001 |
| WO | WO 01/97793 A | 12/2001 |
| WO | WO 01/97793 A2 | 12/2001 |
| WO | WO 02/05849 | 1/2002 |
| WO | WO 02/047493 | 6/2002 |
| WO | WO 02/092073 | 11/2002 |
| WO | WO 02/096408 | 12/2002 |
| WO | WO 02/102757 | 12/2002 |
| WO | WO 03/013276 | 2/2003 |
| WO | WO 03/013497 A | 2/2003 |
| WO | WO 2003/043972 | 5/2003 |
| WO | WO 03/075003 | 9/2003 |
| WO | WO 03/075670 | 9/2003 |
| WO | WO 03/092628 | 11/2003 |
| WO | WO 2004/012753 | 2/2004 |
| WO | WO 2004/024136 | 3/2004 |
| WO | WO 2004/028529 | 4/2004 |
| WO | WO 2004/084882 | 10/2004 |
| WO | WO 2004/105517 | 12/2004 |
| WO | WO 2005/018632 A1 | 3/2005 |
| WO | WO 2005/037848 | 4/2005 |
| WO | WO 2005/063231 | 7/2005 |

OTHER PUBLICATIONS

Suhara Yet al: "Synthesis and biological activities of 2-arachidonoylglycerol, an endogenous cannabinoid receptor ligand, and its metabolically stable ether-linked analogues" Chemical and Pharmaceutical Bulletin, vol. 48, No. 7, Jul. 2000, pp. 903-907.*
Seltzman H H et al: "Facile synthesis and stabilization of 2-arachidonylglycerol via its 1,3-phenylboronate ester" Tetrahedron Letters, vol. 41, No. 19, May 2000, pp. 3589-3592.*
Nakane, S., et al; "Occurrence of a Novel Cannabimimetic Molecule 2-Sciadonoylglycerol (2-Eicosa-5',11',14'-trienoylglycerol) in the Umbrella Pine *Sciadopitys verticillata* Seeds"; *Biological and Pharmaceutical Bulletin*; vol. 23(6), pp. 758-761 (2000) XP-002384246.
Suhara, Y., et al; "Synthesis and Biological Activities of 2-Archidonoylglycerol, an Endogenous Cannabinoid Receptor Ligand, and Its Metabolically Stable Ether-linked Analogues"; *Chemical and Pharmaceutical Bulletin*; vol. 48(7); pp. 903-907 (2000) XP-002384247.
Seltzman, H.H., et al; "Facile synthesis and stabilization of 2-arachidonylglycerol via its 1,3-phenylboronate ester"; *Tetrahedron Letters*; vol. 41; pp. 3589-3592 (2000) XP-004203211.
Awl, R.A., et al; "Synthesis and Characterization of Triacylglycerols Containing Linoleate and Linolenate"; *Lipids*, vol. 24, No. 10, pp. 866-872 (1989).
Sintez Prirodn. Soedin., ikh Analogov I Fragmentov, Akad. Nauk SSSR, Otd. Obshch. I Tekhn. Khim., *Chemical Abstracts*; abstr No. 65:8747b; pp. 16-21 (1965).
Leventhal, L.J., et al; "Treatment of Rheumatoid Arthritis with Gammalinolenic Acid"; *Annals of Internal Medicine*; vol. 119; No. 9; pp. 867-873 (1993).
Fisher, B.A.C., et al; "Effect of omega-6 lipid-rich borage oil feeding on immune function in healthy volunteers"; Biochemistry Society Transactions; Vol. 25; p. 343S (1997).
Wahl, S.M.; "Transforming Growth Factor 13: the Good, the Bad, and the Ugly"; the Journal of Experimental Medicine, Vol. 180; pp. 1587-1590 (1994).
Levin, G., et al; "Differential metabolism of dihomo-γ-linolenic acid and arachidonic acid by cyclo-oxygenase-1 and cyclo-oxygenase-2: implications for cellular synthesis of prostaglandin $E_1$ and prostaglandin $E_2$"; *Biochem. J.*; vol. 365; pp. 489-496 (2002).
Harbige, L.S., et al; "The protective effects of omega-6 fatty acids in experimental autoimmune encephalomyelitis (EAE) in relation to transforming growth factor-beta I (TGF-β) up-regulation and increased prostaglandin $E_2$ ($PGE_2$) production"; *Clin. Exp. Immunol*; vol. 122; pp. 445-452 (2000).
Griffiths, Gareth; et al; "$\Delta^{6-}$ and $\Delta^{12-}$ desaturase activities and phosphatidic acid formation in microsomal preparations from the developing cotyledons of common borage (*Borago officinalis*)"; *Biochem. J.*; vol. 252; pp. 641-647 (1988).
Leventhal, L.J., et al; "Treatment of Rheumatoid Arthritis with Gammalinolenic Acid"; *Annals of Internal Medicine*; vol. 119; No. 9; pp. 867-873 (1993).
Lawson, L.D., et al; "Triacylglycerol Structure of Plant and Fungal Oils Containing γ-Linolenic Acid"; *Lipids*, vol. 23, No. 4, pp. 313-317 (1988).
Harbige, L.S., et al; "Prevention of experimental autoimmune encephalomyelitis in Lewis rats by a novel fungal source of γ-linolenic acid"; *British Journal of Nutrition*, vol. 74, No. 5, pp. 701-715 (1995).
Hoy, Carl-Erik, et al; "Absorption of γ-Linolenic Acid from Borage, Evening Primrose, and Black Currant Seed Oils: Fatty Acid Profiles, Triacylglycerol Structures, and Clearance Rates of Chylomicrons in the Rat"; *γ-Linolenic Acid: Metabolism and Its Roles in Nutrition and Medicine*; AOCS Press, Champaign, IL, pp. 54-65, (1996) XP009035802.
Co-pending U.S. Appl. No. 10/567,778, filed Feb. 9, 2006.
Co-pending U.S. Appl. No. 11/791,606, filed May 25, 2007.
Co-pending U.S. Appl. No. 11/885,255, filed Aug. 29, 2007.
Co-pending U.S. Appl. No. 10/555,757, filed Nov. 7, 2005.
Co-pending U.S. Appl. No. 12/654,780, filed Dec. 31, 2009.
Co-pending U.S. Appl. No. 12/654,779, filed Dec. 31, 2009.
Co-pending U.S. Appl. No. 13/064,647, filed Apr. 6, 2011.
Akoh, C.C.; "Structured lipids—enzymatic approach"; *Inform*; vol. 6:9, pp. 1055-1061 (1995).
Bradley, D.G., "Designer fats; turning scientific advance into consumer benefit"; *Lipid Technology*; pp. 89-91, Jul. 1997.
Christensen, M.S., et al; "Intestinal absorption and lymphatic transport of eicosapentaenoic 9EPA), docosahexaenoic 9DHA), and decanoic acids: dependence on intramolecular triacylglycerol structure"; *Am. J. Clin. Nutr.* vol. 61, pp. 56-61 (1995).
Christensen, M.S., et al; "Absorption of triglycerides with defined or random structure by rats with biliary and pancreatic diversion"; *Lipids*; vol. 30, No. 6, pp. 521-526 (1995).
Decker, E.A.; "The role of stereospecific saturated fatty acid positions on lipid nutrition"; *Nutr. Rev.*; vol. 54, No. 4, pp. 108-110 (1996).
Dehesh, K., "Production of high levels of 8:0 and 10:0 fatty acids in transgenic canola by overexpression of Ch FatB2, a thioesterase cDNA from Cuphea Hookeriana"; *The Plant Journal*; vol. 9, No. 2; pp. 167-172 (1996).
Gurr, M.; "Fat digestion and assimilation"; *Lipid Technology*; pp. 94-97, Jul. 1997.
Hauumann, B.F.; "Structured lipids allow fat"; *Inform* vol. 8, No. 10, pp. 1004-1011 (1997).
Ikeda I., et al; "Lymphatic absorption of structured glycerolipds containing medium-chain fatty acids and linoleic acid, and their effect on cholesterol absorption in rats"; *Lipids*, vol. 26, No. 5, pp. 369-373 (1991).
Jandacek, R.J., et al; "The rapid hydrolysis and efficient absorption of triglycerides with octanoic acid in the 1 and 3 positions and long-chain fatty acid in the 2 position"; *Am J. Clin. Nutr.*; vol. 45, pp. 940-945 (1987).
Jensen, M.M., et al; "Intestinal absorption of octanoic, decanoic, and linoleic acids: Effect of triglyceride structure"; *Ann. Nutr. Metab*, vol. 38, pp. 104-116 (1994).
Kenler A.S., et al; "Early enteral feeding in postsurgical cancer patients"; *Annals of Surgery*; vol. 223, No. 3, pp. 316-333 (1996).
Kennedy, J.P.; "Structured Lipids: Fats of the Future"; *Food Technology*; pp. 76-83 (1991).
Kritchevsky, D.; "Fatty acids, triglyceride structure, and lipid metabolism"; *Nutr. Biochem*, vol. 6, pp. 172-178 (1995).
Kritchevsky, D., et al; "Cholesterol vehicle in experimental atherosclerosis Part 10. Influence of specific saturated fatty acids"; *Exp. Molec. Pathol*; vol. 6, pp. 394-401 (1967).

Kritchevsky, D., et al; "Cholesterol vehicle in experimental atherosclerosis VII. Influence of naturally occurring saturated fats"; *Med. Pharmacol. Exp.*; vol. 12, pp. 315-320 (1965).

Kritchevsky, D. et al; "Cholesterol vehicle in experimental atherosclerosis Part 15. Randomized butter and randomized lard"; *Atherosclerosis*; vol. 27, pp. 339-345 (1977).

Kritchevsky D., et al, "Experimental atherosclerosis in rabbits fed cholesterol free diets. Part 10. Cocoa butter and palm oil"; *Atherosclerosis*; vol. 41, pp. 279-284 (1982).

Kritchevsky, D. et al; "Influence of triglyceride structure on experimental atherosclerosis in rabbits"; *FASEB J* 10, A187 (1996).

Kritchevsky D.,et al; Experimental atherosclerosis in rabbits fed cholesterol free diets 5. Comparison of peanut, corn, butter and cocon ut oils. Exp. Molec. Pathol. 24: 375-391 (1976).

Kritchevsky, D., et al; "Influence of triglyceride structure on experimental atherosclerosis in rabbits"; *FASEB J* 9, A320 (1995).

Kritchevsky, K. D., et al; "Thyroid hormone and experimental atherosclerosis in rabbits"; *Atherosclerosis*; vol. 23, pp. 249-252 (1976).

Kritchevsky, D, et al; "Experimental atherosclerosis in rabbits fed cholesterol free diets 5. Comparison of peanut, corn, butter and coconut oils"; *Exp. Molec. Pathol.*, vol. 24, pp. 375-391 (1976).

Kubow, S., et al; "The influence of positional distribution of fatty acids in native, interesterified and structure-specific lipds on lipoprotein metabolism and atherogenesis"; *Nutr. Biochem*; vol. 7, pp. 530-541 (1996).

Mattson, F.H., et al; "The digestion and absorption of triglycerides"; *J. Biol. Chem.*; vol. 239, pp. 2772-2777 (1964).

Metolli, A.M., et al; "Medium-chain lipds: new sources, uses"; *Inform*; vol. 8, No. 6, pp. 597-603 (1997).

Myher, J.J., et al; "Acylglycerol Structure of peanut oils of different atherogenic potential"; *Lipids*; vol. 12; pp. 765-878 (1977).

Sadou, H. et al; "Differential incorporation of fish-oil eicosapentaenoate and docosahexaenoate into lipds of lipoprotein fractions as related to their glycerol esterification: a short-term (postprandial) and long-term study in healthy humans"; *Am J. Clin Nutr.*; vol. 62, pp. 1193-1200 (1995).

Small, D.M.; "The effects of glyceride structure on absorption and metabolism"; *Annu. Rev. Nutr.*; vol. 11, pp. 413-434 (1991).

Voelker, T.A., et al; "Fatty acid biosynthesis redirected to medium chains in transgenic oilseed plants"; *Science*; vol. 257, pp. 72-74 (1992).

Zock, P.L., et al; "Positional distribution of fatty acids in dietary triglycerides: effects on fasting blood lipoprotein concentrations in humans"; *Am. J. Clin. Nutr.*; vol. 61, pp. 48-55 (1995).

Kritchevsky, D.; "Fatty acids, triglyceride structure, and lipid metabolism"; *Nutr. Biochem*; vol. 6, pp. 172-178 (1995).

Miles, E.A., et al; "The influence of different combinations of γ-linolenic acid, stearidonic acid and EPA on immune function in healthy young male subjects"; *British Journal of Nutrition*; vol. 91, pp. 893-903 (2004).

McCormick, J.N., et al; "Immunosuppressive effect of linolenic acid"; *The Lancet*; p. 508 (1977).

Demmelmair, H., et al; "Influence of formulas with borage oil or borage oil plus fish oil on the arachidonic acid status in premature infants"; *Lipids*, vol. 36, No. 6; pp. 555-566 (2001).

Thijs, C., et al; "Essential fatty acids in breast milk of atopic mothers: comparison with non-atopic mothers, and effect of borage oil supplementation"; *European Journal of Clinical Nutrition*; vol. 54, pp. 234-238 (2000).

Leventhal, L.J., et al; "Treatment of Rheumatoid Arthritis with Blackcurrant Seed Oil"; *British Journal of Rheumatology*; vol. 33, pp. 847-852 (1994).

Zurier, R.B., et al; "Gamma-Linolenic Acid Treatment of Rheumatoid Arthritis"; *Arthritis & Rheumatism*; vol. 39, No. 11, pp. 1808-1817 (1996).

Patent Abstracts of Japan, vol. 1995, No. 01, Feb. 28, 1995 & JP 06 279311 A (Sagami Chem Res Center; others: 01), 04 Oct. 4, 1994 (Abstract).

Patent Abstracts of Japan, vol. 1996, No. 03, Mar. 29, 1996 & JP 07 309773 A (Sagami Chem Res Center; others: 01), Nov. 28, 1995 (Abstract).

Mechoulam, R., et al; "Cannabinoids and brain injury: therapeutic implications"; *Trends in Molecular Medicine*; vol. 8, No. 2; pp. 58-61 (2002) XP-002381881.

Database Biosis (Online), Biosciences Information Service, Philadelphia, PA, USA; Mar. 2003; Rockwell C.E., et al; "Inhibition of interleukin-2 (IL-2) by the endogenous cannabinoid, 2-arachidonyl glycerol, is partly mediated through peroxisome proliferators-activated receptor-gamma (PPAR-gamma)"; Database accession No. PREV200300230725 abstract & *Toxicological Sciences*, vol. 72, No. s-1, Mar. 2003, p. 328, 42$^{nd}$ Annual Meeting of the Society of Toxicology; Salt Lake City, UT, USA; Mar. 9-13, 2003, ISSN: 1096-6080.

Database Embase (Online) Elsevier Science Publishers, Amsterdam, N1; 2005, Kaplan, B. L.F., et al; "2-Arachidonoyl-glycerol suppresses interferon-γ production in phorbol ester/ionomycin-activated mouse splenocytes independent of CB1 or CB2", XP-002381886 (abstract); *Journal of Leukocyte Biology*; vol. 77 pp. 966-974 (2005).

Ouyang, Y., et al; "Suppression of Interleukin-2 by the Putative Endogenous Cannabinoid 2-Arachidonyl-Glycerol is Mediated through Down-regulation of the Nuclear Factor of Activated T Cells"; *Molecular Pharmacology*; vol. 53, pp. 676-683 (1998) XP-002381882.

Venderova, K., et al; "Differential effects of endocannabinoids on [$^3$H]-GABA uptake in the rat globus pallidus"; *Experimental Neurology*; vol. 194, pp. 294-287 (2005).

The Merk Manual, Fifteenth Edition, pp. 1421-1424 (1987).

A copy of Merk Manual regarding Alzheimer's Disease. 1987.

Yuksel et al; "Etiologic classification of 4659 patients with mental retardation or multiple congenital abnormality and mental retardation"; *J. Pewdiatr. Neurosci.*, pp. 45-52 (2007).

Yaqoob, P., et al; "Encapsulated fish oil enriched in α-tocopherol alters plasma phospholipid and mononuclear cell fatty acid compositions but not mononuclear cell functions"; *European Journal of Clinical Investigation*; vol. 30; pp. 260-274 (2000).

* cited by examiner

2-γ- Linolenoyl glycerol formal(2-GLA MGF)

CYTOKINE MODULATORS USING CYCLIC GLYCERIDES OF ESSENTIAL POLYUNSATURATED FATTY ACIDS

This application is a continuation of application Ser. No. 11/885,254 filed Jul. 16, 2008 now abandoned, which is a 371 of PCT/GB2006/000779 filed Mar. 2, 2006, which claims priority to British Application No. 0504362.5 filed Mar. 2, 2005, the entire contents of each of which are hereby incorporated by reference.

The present invention relates to a method for treating diseases and disorders in which cytokines are in state of imbalance or otherwise capable of modulation to provide therapeutic benefit. Particularly the invention provides a method of treatment of patients in need of therapy for disorders where the cytokines TGF-$\beta$1, TNF-$\alpha$, IL-1$\beta$, IL4, IL5, IL6, IL8, IL10, IL13, and $\gamma$-IFN are dysregulated or capable of modulation to provide therapeutic benefit.

Particular diseases that are treatable by the present method are disorders such as abnormalities of the immune system, for example systemic lupus erythematosus (SLE), allergy, asthma, crohn's disease and rheumatoid arthritis, but particularly multiple sclerosis, and also neurodegenerative diseases such as sequelae of stroke, head trauma, bleeds and the chronic abnormalities of Alzheimer's and Parkinson's disease. Further disorders that can be pretreated both prophylactically and therapeutically are coronary heart disease (CHD) abnormalities of pre-mature infants and sepsis.

The inventor's copending patent application WO2004/100943 and WO2005/018632, incorporated herein by reference, relate to the use of synthetic, plant and fungal oils for the treatment of neurodegenerative diseases, particularly multiple sclerosis, stroke, head trauma, Alzheimer's and Parkinson's disease. WO2004/100943 relates to oils characterised by having at high percentages of the essential fatty acid $\gamma$-linolenic acid (GLA) at the sn-2 position of their lipids, typically being over 40% of the sn-2 fatty acid total of the oil. WO2005/018632 relates to structured lipids having an sn-2 fatty acid residue selected from $\gamma$-linolenic acid (GLA), dihomo-$\gamma$-linolenic acid (DHGLA) and arachidonic acid (AA).

It is well reported in the literature that essential fatty acids (EFAs) of the n-3 and n-6 unsaturation pattern have beneficial effect in a wide variety of human physiological disorders, including autoimmune disease (WO 02/02105). Harbige (1998) Proc. Nut. Soc. 57, 555-562 reviewed the supplementation of diet with n-3 and n-6 acids in autoimmune disease states, and particularly noted evidence of benefit of $\gamma$-linolenic (GLA) and/or linoleic acid (LA) rich oils.

Cytokines are implicated in the pathogenesis of MS, with many studies showing an increase in myelinotoxic inflammatory cytokines (TNF-$\alpha$, IL-1$\beta$ and IFN-$\gamma$) coinciding with the relapse phase of the disease. Conversely, levels of the anti-inflammatory and immunosuppressive cytokine transforming growth factor-beta1 (TGF-$\beta$1) appear to be reduced during a phase of relapse and increase as the patient enters remission. Thus the balance between biologically active TGF-$\beta$1 and the pro-inflammatory TNF-$\alpha$, IL-1$\beta$ and IFN-$\gamma$ appears to be dysregulated during MS relapse-remission.

During natural recovery phase from EAE, TGF-$\beta$1-secreting T-cells inhibit EAE effector cells, TGF-$\beta$1 is expressed in the CNS and, in oral-tolerance-induced protection in EAE, TGF-$\beta$ and PGE$_2$ are expressed in the brain (Karpus & Swanborg (1991); Khoury et al (1992)). Harbige ((1998) concluded that dietary $\gamma$-linolenic acid effects on EAE are mediated through Th$_3$-like mechanisms involving TGF-$\beta$1 and possibly through superoxide dismutase antioxidant activity.

Borage oil (typically 20% to 23% $\gamma$-linolenic acid and 34 to 40% linoleic acid per 100% fatty acid content) and *Mucor javanicus* fungal oil (see FIG. 1) have been shown to be effective in the EAE animal model used to identify MS candidates, whilst never having been shown to be significantly effective in the human disease. High levels of linoleic rich oil containing low levels of $\gamma$-linolenic acid (EPO: linoleic acid: $\gamma$-linolenic acid 7:1) partially suppressed the incidence and severity of EAE in rat (Martin & Stackpoole, 1978) whereas the Bates' Naudicelle study referred to above led to worsening of patients. In spite of the use of Borage oil and other GLA/LA containing oils such as Evening Primrose oil by multiple sclerosis sufferers over the past 30 years or so, the vast majority of patients fail to recover from the disease, showing no significant improvement, with the underlying disease continuing to progress to death.

It has been suggested to use, inter alia, $\gamma$-linolenic acid and linoleic acid rich Borage oil as a means to provide immunosuppression in multiple sclerosis (U.S. Pat. No. 4,058,594). Critically, the dose suggested is 2.4 grams of oil per day and no actual evidence of efficacy is provided. This is much lower than the low 5 g/day dose found to be ineffective in vivo in man in the WO2004/100943 study.

Other more dramatic immunosuppressant treatments, including T cell depleters and modulators such as cyclophosphamide, are also shown to be effective in the EAE model, but where these are employed in the human multiple sclerosis disease symptoms improve, but the underlying disease continues to progress. T-cells indeed produce beneficial cytokines, such as TGF-$\beta$1, as well as deleterious ones in man. David Baker of Institute of Neurology, UK summed up the disparity between what is effective in the EAE and in MS with a paper entitled '*Everything stops EAE, nothing stops MS*' at the 10th May 2004 UK MS Frontiers meeting of the UK MS Society.

In the WO2004/100943 study the present inventors Harbige and Leach, with coinventor Sharief, surprisingly determined that with compliance to a 'high dose' treatment with triglyceride oil containing high levels of sn-2 $\gamma$-linolenic acid (>40% of residues at the sn-2 being of $\gamma$-linolenic acid) with suitable accompanying fatty acid content, remarkable levels of improvement in almost all symptoms of MS can be achieved, way surpassing that provided by the current gold standard treatment. Such success is particularly surprising in the light of the prior use of other $\gamma$-linolenic acid containing preparations without success, such as the Naudicelle study.

The WO2004/100943 study shows that over an 18-month period, patients taking high dose (15 g/day) selected high sn-2 $\gamma$-linolenic acid borage oil showed significant ($p<0.001$) and marked improvements in EDSS score, a reduced rate of relapse, symptomatic relief of muscle spasticity and painful sensory symptoms, and improved objective measures of cognitive functions. Low doses of 5 g/day of this borage oil were without effect.

Patients taking the highest dose of this borage oil maintained their level of peripheral blood mononuclear cell production (PBMC) of TGF-$\beta$1 during the trial period, their pro-inflammatory cytokines TNF-$\alpha$ and IL-1$\beta$ were significantly and markedly (<70%) reduced and they either maintained or increased the PBMC membrane long chain omega-6 fatty acids dihomo-$\gamma$-linolenic acid (DHLA) and arachidonic acid (AA) in contrast to patients taking placebo who demonstrated loss of these fatty acids over the course of the trial period.

Thus whilst immuno-suppression would be expected to reduce increase of active lesioning and neurodegeneration, the high sn-2 GLA oil treatment apparently targeted maintenance and/or increase of key membrane lipid components that are otherwise specifically lost in MS, being consistent with a correction of a metabolic defect not otherwise effectively treated by current therapies. The fact that the low dose (5 grams/day) had no effect on this supports such determination.

The present inventors now set out, in view of the results obtained with high sn-2-γ-linolenic acid Borage Oil, to demonstrate that it is indeed the presence of an sn-2-γ-linolenic acid, dihomo-γ-linolenic acid or arachidonic acid residue in a monoglyceride, particularly an sn-2 monoglyceride, or a metabolic precursors thereof, that gives it efficacy in treating cytokine dysregulation. Noting that the triglycerides themselves are of nearly three times the weight, and thus dose, of monoglyceride counterparts, they have determined that it is possible to administer essential fatty acids of the n-3, n-6 and n-9 type, particularly the n-6 type, as metabolic precursors or analogues of sn-2 monoglycerides and still obtain beneficial cytokine changes. Particularly these compounds are believed to be more stable than the equally less bulky monoglycerides.

It has been reported that 2-arachidonyl glycerol has activity in decreasing TNF-α and reactive oxygen species induced disease (see WO 01/97793), however, the corresponding γ-linolenoyl and palmitoyl compounds are said to be inactive. An sn-2-arachidonyl structured lipid has further been reported to be active in 'brain hypofunction' such as in mild cognitive impairment (see EP 1419768).

The dose advantages of use of monoglycerides over triglycerides may be offset in part by possible increased instability of certain forms as compared with the sn-1, sn-3 saturated acyl group sn-2 EFA triglyceride exemplified in PCT/GB2004/003524. Such instability may be due e.g. to transesterification and oxidation. This issue may be addressed by producing the monoglyceride in a more stable form, e.g. a solid or semi solid rather than a liquid oil.

The present inventors have now further provided compounds, known and novel, which may be metabolic precursors of the monoglyceride as claimed below that are either metabolised to give that form in vivo, or are directly active, but which resist transesterification and other degradations in storage.

Preliminary studies by the inventors have shown that the compounds selected for the use of the present invention are more resistant to degradation by at least some mammalian lipases than the previously used triglyceride based Borage, Evening Primrose and structured lipids and more resistant to rearrangement than monoglycerides.

These compounds are particularly cyclic glycerols bearing essential fatty acids, particularly n-3, n-6 and n-9, but particularly n-6 fatty acids, in a position equivalent to the on-2 position on the glycerol. The inventors have determined that these compounds are capable of regulating cytokines in a favourable manner to patient health based upon their previous clinical studies with Borage oil and the structured lipid in vivo and in vitro work.

Cyclic glycerols are known as a class eg see. Chem Abstracts no 65:8747b and have been used as intermediates in the synthesis of monoacylglycerides eg see Chemical & Pharmaceutical Bulletin (2000), 48(7) 903-907. Recently US2005/0020679 has proposed that all members of this class bearing a polyunsaturated fatty acyl group, particularly an arachidonyl group, have been proposed as having utility as anandamide transport inhibitors having pharmacological use in treatment of pain, peripheral pain, glaucoma, epilepsy, nausea, AIDS wasting, cancer, neurodegeneration, Multiple Sclerosis, Parkinson's Disease, Huntington's Chorea and Alzheimer's disease, enhancement of appetite, reduction of fertility, Tourettes and other motor function disorders, for neuroprotection, peripheral vasodilation and suppress memory.

This document and its predecessor WO99/64389 (directed to analgesia) provide no teaching of the particular compounds of the present invention and significantly teaches that a therapeutically effective amount of cyclic glycerol is 10 mg/day to 1000 mg/day. The present inventors studies on relative effect in animals and on cells has led them to determine that such a dose will be ineffective in the cytokine regulating indication now disclosed. The effective dose in man is expected to be above 1000 mg/day, particularly between 14 to 10 g per day. More preferably being 2 to 6 g/day, still more preferably 2 to 4 g/day.

Without the cytokine regulation such dosages provide, treatment of diseases such as demyelinating diseases Multiple Sclerosis and Alzheimer's, Parkinson's, Huntingdon's Chorea and trauma and stroke with a view to halting ongoing immune cell and cytokine destruction of tissues cannot be achieved. Mere enhancement of natural anandamide levels by blocking reuptake cannot provide relief where natural anandamide is not present in effective amount, e.g. in T-cells and around CNS lesions.

In a first aspect the present invention provides a method of treating a patient in need modulation of cytokines, particularly TGF-β1, TNF-α, IL-1β, IL4, IL5, IL6, IL8, IL10, IL13 and/or γ-IFN, comprising administering to that patient a therapeutically effective dose of a compound of general formula I

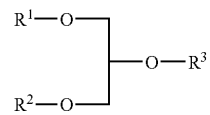

wherein $R^1$ and $R^2$ together form a group

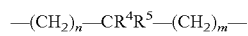

—(CH$_2$)$_n$—CR$^4$R$^5$—(CH$_2$)$_m$— wherein n and m are independently selected integers 0, 1 or 2 and $R^4$ and $R^5$ are independently selected from H, $C_{1-18}$ alkyl, $C_{1-18}$ alkoxy, $C_{1-18}$ hydroxyalkyl, $C_{2-18}$ alkenyl and $C_{6-18}$ aryl or aralkyl and $R^3$ is the a fatty acyl group of an essential polyunsaturated fatty acid.

Preferred polyunsaturated fatty acyl groups are those of n-3, n-6 and n-9 fatty acids, more preferably n-3 and n-6 fatty acids, still more preferably being γ-linolenoyl, γ-dihomolinolenoyl and arachidonoyl.

Preferably $R^1$ and $R^2$ are selected from H or a group —CR$^4$R$^5$ where R$^4$ and R$^5$ are independently selected from H and $C_{1-6}$ alkyl. Most advantageously $R^1$ and $R^2$ form a group —CH$_2$— or —CH$_2$CH$_2$—.

Particularly preferred are compounds that are 5-essential fatty acyloxy-1,3-dioxans, more particularly n-3-fatty acyloxy or n-6 fatty acyloxy-1,3-dioxans, most preferably 5-γ-linolenoyloxy, 5-dihomo-γ-linolenoyloxy and 5-arachidonoyloxy-1,3-dioxans. Most preferable are the non-inflammatory 5-'γ-linolenoyloxy and 5-dihomo-γ-linolenoyloxy-1,3-dioxans.

Particularly treated are dysregulated cytokine abnormalities of the immune system, for example diseases such as systemic lupus erythematosus (SLE), allergy, asthma, crohn's disease and rheumatoid arthritis, but particularly multiple sclerosis, and also neurodegenerative diseases such as sequelae of stroke, head trauma, bleeds and the chronic abnormalities of Alzheimer's and Parkinson's disease. Further disorders that can be pretreated both prophylactically and therapeutically are coronary heart disease (CHD) abnormalities of pre-mature infants and sepsis.

Particularly advantageously treated neurodegenerative diseases are those involving demyelination. The present method is specifically addressed at arresting underlying neurodegeneration and restoring neuronal function. Particularly the method preferably normalises neuronal membrane composition, and restores healthy PBMC stimulated or spontaneously released TGF-β1/TNFα ratios and the ratios of TGF-β1 with other PBMC released cytokines. Most advantageously the method arrests neurodegeneration in multiple sclerosis of all types but particularly relapsing remitting, primary progressive and chronic progressive MS and the restoration, in part or completely, of neuronal function such as measured, eg. By MRI or CAT scan or by EDSS score. Such method may also be used in treatment of cerebral impairment after stroke, head trauma and intracranial bleeding where there is demyelination or neuronal damage. Further application is provided in treating other chronic demyelination such as in Alzheimer's and Parkinson's disease.

Preferably the compound of the present invention is administered for a duration and at a dose sufficient to maintain or elevate TGF-β1 levels in the patient to therapeutic levels. By therapeutic levels is meant levels at least consistent with healthy subjects. Preferably the dose is such as to produce a TGF-β1/TNF-α ratio spontaneously released from peripheral blood mononuclear cells (PBMCs) isolated from blood of a patient, after 18 months of daily dosing, of 0.4 to 3.0, at least 0.5, more preferably at least 0.75 and most preferably at least 1. Preferably the dose is such as to produce a TGF-β1/IL-1β ratio in blood of a patient, after 18 months of daily dosing, of at least 0.5, more preferably at least 0.75 and most preferably at least 1. Preferably said levels are produced after 12 months and more preferably after 6 months.

The present invention further provides a method of treating a patient in need of remyelination in a demyelinating disease comprising administering to that patient a therapeutically effective amount of a compound of formula I wherein $R^3$ is selected from γ-linolenoyl, γ-dihomolinolenoyl and arachidonoyl; most preferably γ-linolenoyl and γ-dihomolinolenoyl.

For all the methods of the invention, the amount of compound administered daily will be between 0.5 and 30 grams, orally dosed, still more preferably between 0.75 and 20 grams and most preferably between 1 and 18 grams, typically 2 to 5 grams. This dose may be given as one single dose or in two or more doses together totally this amount per day.

Where the sn-2 moiety is that of a γ-linolenic acid residue, the dose may be toward the higher end of these ranges, but is preferably between 1 and 10 grams/day, more preferably 2 to 6 grams/day. Where the sn-2 moiety is that of a dihomo-γ-linolenic acid residue, the dose may be less, whilst where the sn-2 moiety is that of an arachidonic acid residue, efficacy is higher, but dosing should be more cautious, due to possibilities of unwanted side effects at higher levels and the pro-inflammatory nature of this PUFA.

A second aspect of the present invention provides novel compound of formula I

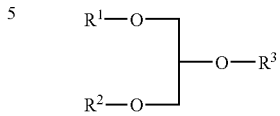

wherein $R^1$ and $R^2$ together form a group

—(CH$_2$)$_n$—CR$^4$R$^5$—(CH$_2$)$_m$— wherein n and m are independently selected integers 0, 1 or 2 and $R^4$ and $R^5$ are independently selected from H, $C_{1-18}$ alkyl, $C_{1-18}$ alkoxy, $C_{1-18}$ hydroxyalkyl, $C_{2-18}$ alkenyl and $C_{6-18}$ aralkyl and $R^3$ is a fatty acyl group of an essential polyunsaturated fatty acid.

Preferred polyunsaturated fatty acyl groups are those of n-3, n-6 and n-9 fatty acids, more preferably n-3 and n-6 fatty acids, still more preferably being γ-linolenoyl, γ-dihomolinolenoyl and arachidonyl.

Preferably $R^1$ and $R^2$ form a group —CR$^4$R$^5$ where $R^4$ and $R^5$ are independently selected from H and $C_{1-6}$ alkyl. Most advantageously $R^1$ and $R^2$ form a group —CH$_2$— or —CH$_2$CH$_2$—.

Thus compounds of formula IIa are preferred

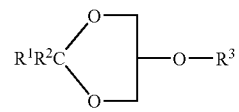

wherein $R^1$ and $R^2$ are independently selected from hydrogen and $C_{1-6}$ alkyl.

Particularly preferred are compounds that are 5-acyloxy-1,3-dioxans, more particularly n-3-fatty acyl or n-6 fatty acyloxy-1,3-dioxans, most preferably 5-γ-linolenoyloxy, 5-dihomo-γ-linolenoyloxy and 5-arachidonoyloxy-1,3-dioxans.

A third aspect of the present invention provides a method for synthesis of a compound of general formula II comprising reaction a 5-hydroxy-1,3-dioxan with an essential fatty acid or an essential fatty acid halide.

A fourth aspect of the present invention provides compositions for use in the method of the present invention comprising the compounds of formula I together with a pharmaceutically or nutraceutically acceptable carrier, coating, capsule, diluent and/or preservative. The compounds for use in the present invention may be administered by any of the conventional vehicles known in pharmacy. Most conveniently they are administered as neat oils or in admixture with foodstuffs, in the form of capsules containing such oils, or in enterically coated forms. Other forms will occur to those skilled in the art but Remington Pharmaceutical Sciences 19$^{th}$ Edition By preservative is meant an antioxidant or inhibitor of transesterification. It is particularly preferred that the composition does not include Vitamin E, or includes only levels of Vitamin E that are 0.05 mg/g or less, e.g. 0.005 to 0.05 mg/g.

A fifth aspect of the present invention provides a pharmaceutical composition for regulating the immune system, particularly by modulating cytokines TGF-β1, TNF-α, IL4, IL5, IL6, IL8, IL10, IL13, and/or γ-IFN comprising a compound of general formula I as defined for the method of treatment of the invention.

A sixth aspect of the present invention provides use of the compounds of formula I, formula H and formula Ha as described above for the manufacture of a medicament for the treatment of cytokine dysregulation and neurodegenerative diseases as set out for the method of the invention. Particularly preferred medicaments are for the arresting and reversing of neurodegeneration in multiple sclerosis of all types but particularly relapsing remitting, primary progressive and chronic progressive and the restoration, in part or completely, of neuronal integrity function such as measured, eg. By MRI or CAT scan or by EDSS score. Other TGF-β1 responsive diseases may be treated as set out previously. Particularly treated is demyelination.

It will be realised by those skilled in the art that other beneficial agents may be combined with the compounds for use in the present invention or otherwise form part of a treatment regime. These might be ion channel blockers, e.g. sodium channel blockers, interferons (α, β, or γ), T-cell depleters, steroids or other palliative agents. It will further be realised that where the immune and inflammatory responses are being modulated, such combinations will need to be made carefully, given the complex nature of these systems. However, given the potential for delayed response to the present compounds, shorter acting agents might be beneficial in the first months of treatment before the cytokine levels are normalised, as long as the additional treatment does not impede this normalization process.

The synthesis of compounds and compositions for use in the present invention is described below together with synthesis of comparative examples. Whilst the Examples exemplify compounds where $R^3$ is γ-linolenoyl, the dihomo-γ-linolenoyl and arachidonoyl and n-3 and n-9 analogues of these are readily synthesised through analogous starting materials.

The present invention will now be described by way of Example only by reference to the following non-limiting Tables, Examples and Figures. Further embodiments falling within the scope of the invention will occur to those skilled in the art in the light of these.

TABLES

EXAMPLES

Background

High sn-2 Borage Oil (WO2004/100943) Trial
Isolation and Culture of PBMC

Heparinised whole blood was diluted with an equal volume of Hanks' balanced salt solution (Sigma, UK) and the resulting diluted blood layered onto Lymphoprep (Nycomed, Oslo, Norway). Following density centrifugation at 800 g for 30 minutes the PBMC were removed from the interface and diluted in Hanks' solution. The cells were then washed twice by centrifugation for 10 minutes at 250 g. The resulting final pellet was then resuspended in culture medium consisting of RPMI-1640 medium (Sigma, UK) supplemented with 2 mM L-glutamine, 100 U penicillin and 100 µg streptomycin (Sigma, UK) and 10% autologous plasma. $2\times10^6$ per ml PBMC, >95% viable as judged by trypan blue exclusion, were added to tissue culture tubes (Bibby Sterilin Ltd, Stone, UK) and incubated for 24 h at 37° C. with 5% $CO_2$. The concentration of antigen, cell density and time of culture were all determined in previous kinetic experiments to determine maximum cytokine production (data not shown). Routine cytospin preparations were also prepared for subsequent differential counts. Following incubation the cells were removed from culture by centrifugation at 250 g for 10 minutes, the resulting supernatants were then removed, aliquoted and stored at −70° C.

Preparation of Plasma Samples 10 ml of heparinised blood was spun at 250 g for 10 minutes. The resulting plasma layer was then removed, aliquoted and stored at −70° C.

Detection of Pro-Inflammatory Cytokines

TNF-α, IL-1β and IFN-γ in cell culture, supernatants and plasma were detected using commercially available paired antibodies enabling cytokine detection in an ELISA format (R&D systems Ltd, Abingdon, UK). The sensitivities for the TNF-α and IFN-γ ELISAs were 15.6-1000 pg/ml and 3.9-250 pg/ml for IL-1β.

Detection of Biologically Active TGF-β1

Biologically active TGF-β1 in cell culture supernatants and plasma were detected using the commercially available $E_{max}$ ELISA system with a sensitivity of 15.6-1000 pg/ml (Promega, Southampton, UK).

Statistical Analysis

Differences in cytokine production were compared using Student's t-test and Mann-Whitney U-test and were considered significant when p values were less than 0.05.

Results

Figure 1:
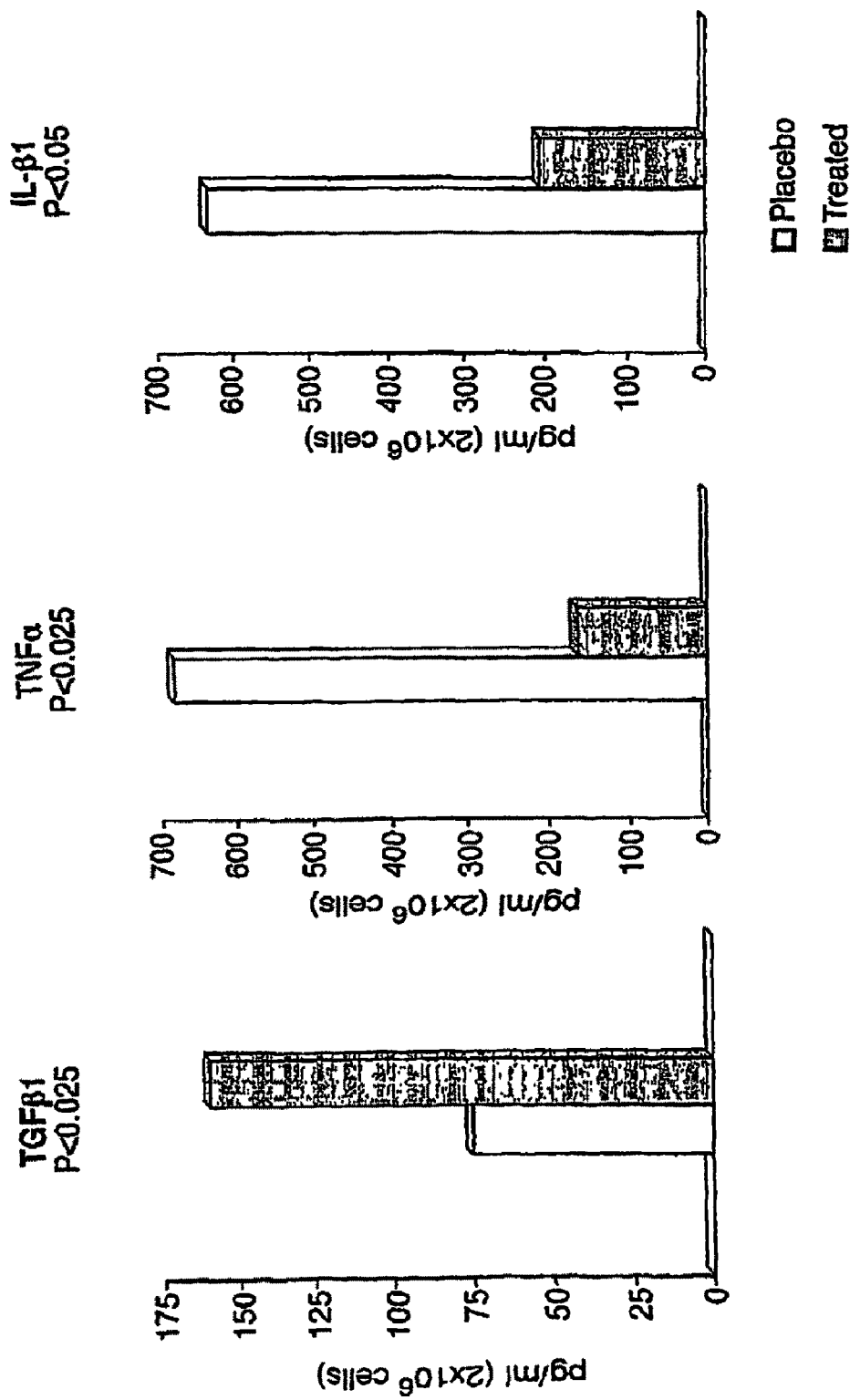
FIG. 1: Shows spontaneous peripheral blood mononuclear cell cytokine production in placebo and high sn-2 γ-linolenic acid, WO2004/100943 trial oil treated human MS patients at 18 months. The left hand column in each case is placebo: right treated.
Figure 2:
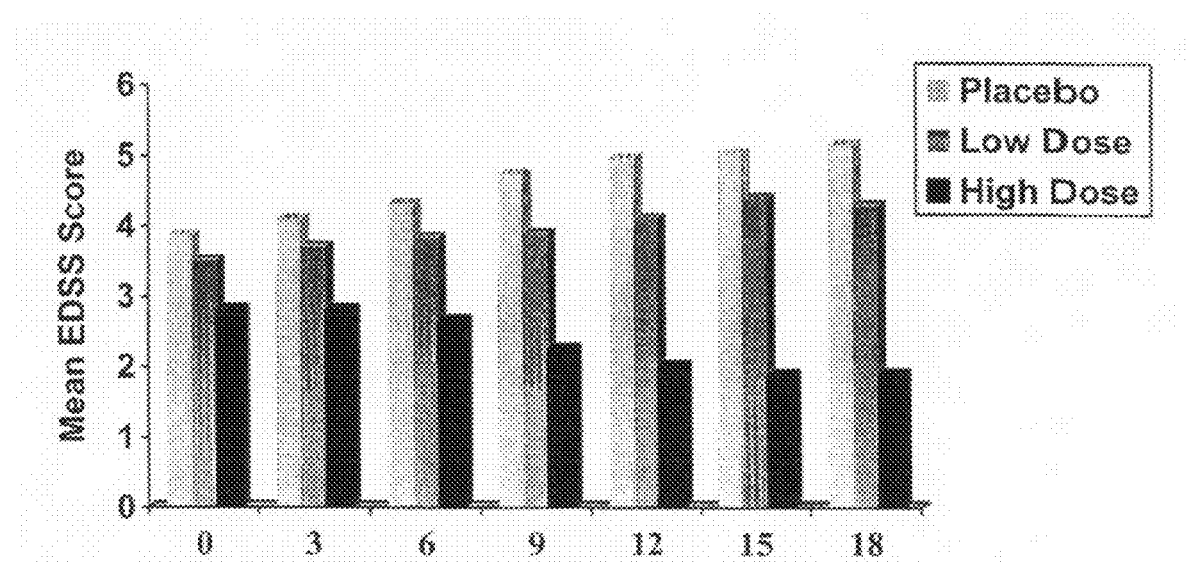
FIG. 2: Shows the effect of placebo and low dose (5 g/day) high sn-2 GLA Borage oil on human MS patient EDSS score as compared to high dose (15 g/day) displayed as a histogram with months treatment on the x axis.
Figure 3:
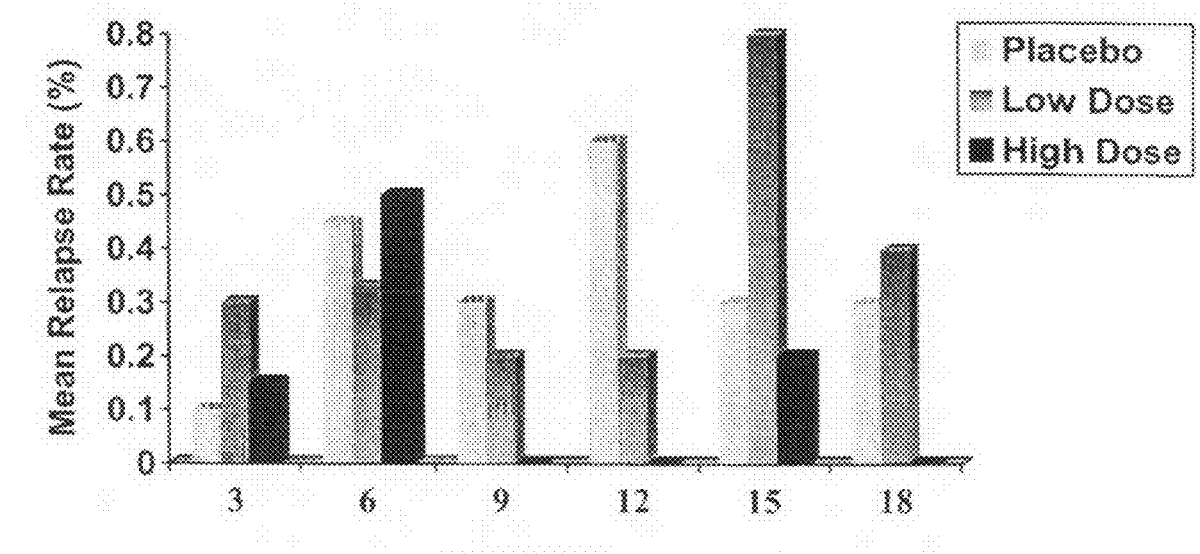
FIG. 3: Shows the effect of placebo, low dose and high dose high sn-2 GLA Borage oil on human MS patient Mean Relapse rate (%) as histogram with months on x axis.
Figure 4:
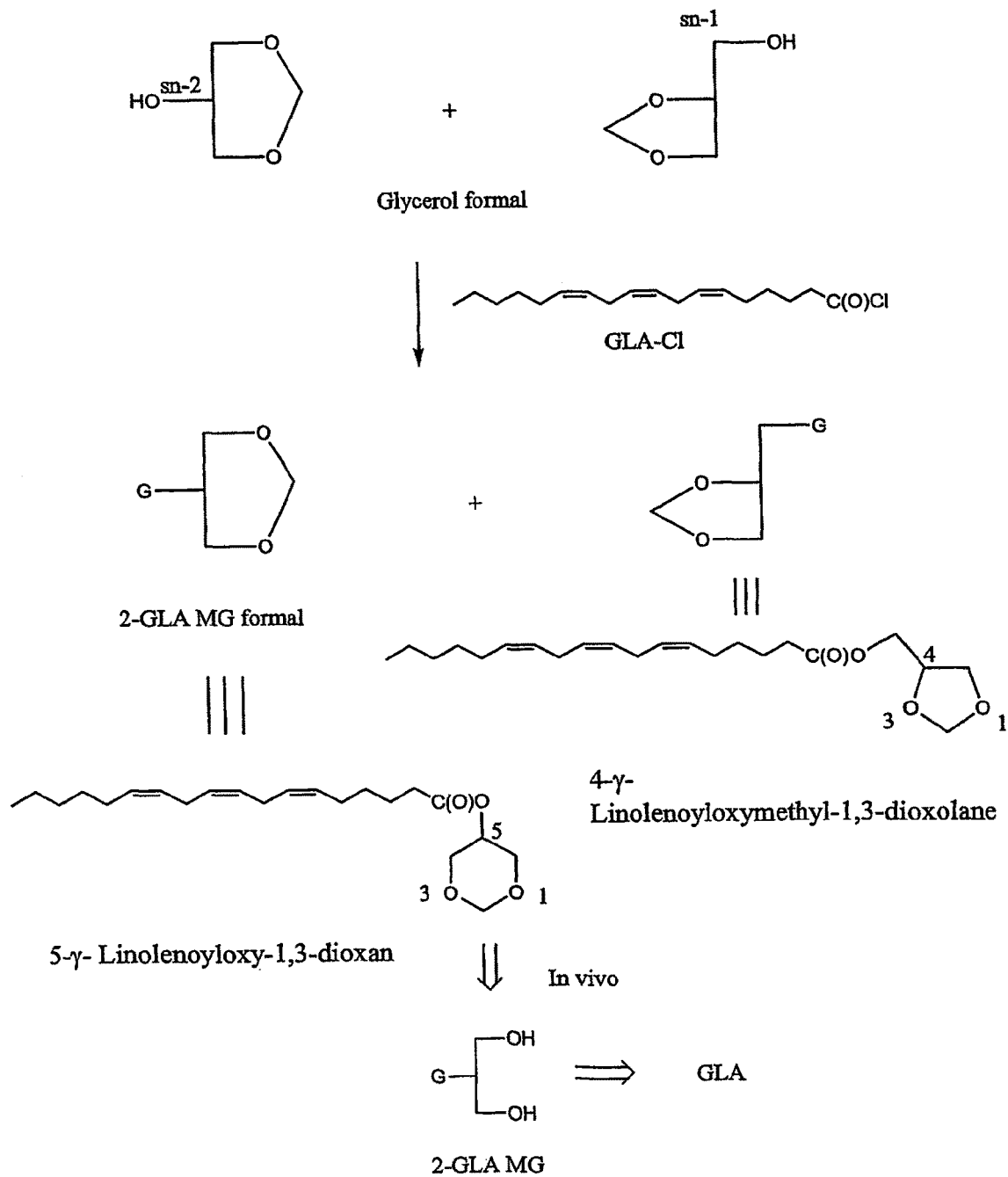
FIG. 4: Shows synthesis of 2-GLA glycerol formal (aka: 5-γ-linolenoyloxy)-1,3-dioxan and 5-(1,3-dioxanyl)methyl-γ-linolenate)

See FIG. 1

Experimental Procedure

The proton-decoupled $^{13}C$ NMR spectra with suppressed NOE were collected at 21° C. in a 5-mm broadband probe on a Joel 500 MHz spectrometer operating at 125.728 MHz. Waltz decoupling was the chosen mode of decoupling and was gated on only during the 14.89 s acquisition time. The relaxation delay was set at 30 secs and the pulse angle was 90°. The spectral window used was ca.35 ppm (from 173.5 to 172.6 ppm) with a 170 ppm offset. The spectra were internally referenced to $CDCl_3$ at 77.0 ppm. Typically, the approximate number of scans collected for adequate signal-to-noise ranged from 300 to 1200 scans depending on the concentration and purity of the sample. The total acquisition time for the experiments ranged between 2-8 h e.g. 1272 scans; data points 65,536. Concentrated solutions up to 20% w/v were employed when possible to reduce the acquisition time The chemical shifts quoted vary with the concentration of the solution.

Synthesis of Compounds for Use in the Present Invention

Example 1

1a) Preparation of 1,3-O-benzylidene glycerol 2-octa-6Z, 9Z, 12Z-trienoate (Intermediate and Known Compound for Use in the Invention where R4 is H and R5 is Benzyl)

Oxaloyl chloride (7.8 ml, 11.3 g, 0.089 mol, 0.95 equivalents) was added over 2-3 minutes to a stirred solution of γ-linolenic acid (GLA95, 16.7 g, 0.060 mol, 0.64 equivalents-Scotia) in dichloromethane (100 ml) under $N_2$. The mixture was stirred overnight at room temperature and then concentrated in vacuo to give a tan oil. This crude γ-linolenoyl chloride was added over ca 10 minutes to a stirred solution of 1,3-O-benzylidene glycerol (13.0 g, 0.094 mol, 1 equivalent), dry pyridine (30 ml, 29.3 g, 0.37 mol, 4 equivalents) and dichloromethane (DCM, 120 ml) at 5° C. and the mixture then stirred at room temperature for 2 hours. The reaction mixture was filtered and then the filtrate washed with DCM. The combined filtrate and washings were then washed with water (2×20 ml) and the DCM extract dried over Mg SO4 and concentrated in vacuo to give a crude product as a tan oil (purity >90% by HPLC). The oil was purified by column chromatography on silica gel (300 g). Elution with DCM gave the product as a yellow oil (19.2 g (73%), 96.3% purity by HPLC).

Example 2

2-GLA Glycerol Formal (aka: 5-γ-linolenoyloxy)-1, 3-dioxan and 5-(1,3-dioxanyl)-methyl-γ-linolenate)

For the purposes of this exemplification, the synthesis of this ester was carried out by acylation of the commercially available glycerol formal mixture using γ-linolenoyl chloride. By this method a mixture of two products is formed and these were separable by column chromatography. The undesired by-product is eluted off the column first; further elution gives the desired acetal-ester. It is a yellow oil at room temperature and appears to have stability properties similar to GLA, stable in air at room temperature for short periods (days) but is best stored long term in a cool place under nitrogen.

Experimental

Oxalyl chloride (2.6 nil, 3.78 g, 30 mmol, 1.5 equiv) was added to a solution of γ-linolenic acid (GLA, 5.56 g, 20 mmol. 1.0 equiv) in dichloromethane (DCM, 40 ml). The resulting solution was stirred under $N_2$ at room temperature overnight and then concentrated in vacuo. The residual oily γ-linolenoyl chloride was added dropwise over 10 min to a stirred solution of glycerol formal (2.50 g, 24 mmol, 1.2 equiv) in DCM (40 ml) containing pyridine (10 ml, 9.78 g, 0.12 mol, 6 equiv) at 5° C. The reaction mixture was stirred at room temperature for 2 h, the precipitated pyridine hydrochloride filtered off, and the filtrate washed with water (2×). After drying over $MgSO_4$ the solvent was removed in vacuo to give a light tan oil (6.5 g). This material was chromatographed on silica (60 g). Elution with hexane-ether (94:6) gave 5.2 g of an oil consisting of two components (TLC, HPLC). These were separated on a second silica column (60 g). Elution with hexane-ether (98:2 then 95:5) gave 4-(γ-linolenoyloxymethyl)-1,3-dioxolane as a yellow oil (1.2 g, 98% by HPLC). $δ_H$ (500 MHz, $CDCl_3$) 0.89 (3H, t, J=7.0 Hz, $CH_3$), 1.24-1.45 (8H, complex in, 4×$CH_2$), 1.65 (2H, p, J=7.5 Hz, $CH_2$—C—CO), 2.08 (4H, m, 2×$CH_2C$=C), 2.35 (2H, t, =7.5 Hz, $CH_2CO$), 2.80 (411, t, J=6.0 Hz, 2×C=$CCH_2C$=C), 3.67 (1H, m, $OCH_AH_B$), 3.97 (1H, m, $OCH_AH_B$), 4.14 (2H, m, $OCH_AH_B$), 4.26 (1H, p, J=3.5 Hz, CHO), 4.89 and 5.02 (2H, 2×s, $OCH_2O$), 5.36 (6H, in, 3×CH=CH). $δ_C$ (126.8 MHz, $CDCl_3$) 14.09 ($CH_3$), 22.60, 24.51, 25.65, 26.85, 27.23, 29.16, 29.34, 31.53, 33.97, 63.93 ($CH_2O$), 66.72 ($CH_2O$), 73.31 (CHO), 95.44 (OCO), [127.60, 128.04, 128.32, 128.41, 129.50, 130.41, olefinic C], 173.26 (carbonyl).

Further elution gave 5-(γ-linolenoyloxy)-1,3-dioxan as a yellow oil (1.6 g, 97.8%) by HPLC). $δ_H$ (500 MHz, $CDCl_3$) 0.89 (3H, t, J=7.0 Hz, $CH_3$), 1.24-1.46 (8H, complex m, 4×$CH_2$), 1.67 (2H, p, J=7.5 Hz, $CH_2$—C—CO), 2.05 (4H, m, 2×$CH_2C$=C), 2.40 (2H, t, J=7.5 Hz, $CH_2CO$), 2.81 (41-1, t, J=6.0 Hz, 2×C=$CCH_2C$=C), 3.91 (2H, m, $OCH_2$), 3.99 (2H, m, $OCH_2$), 4.73 (1H, p, J=3.5 Hz, CHO), 4.80 (1H, d, J=6.0 Hz, $OCH_AH_BO$), 4.93 (1H, d, J=6.0 Hz, $OCH_AH_BO$), 5.37 (6H, m, 3×CH=CH). $δ_C$ (126.8 MHz, $CDCl_3$) 14.08 ($CH_3$), 22.59, 24.53, 25.65, 26.86, 27.22, 29.06, 29.34, 31.52, 34.12, 65.54 (CHO), 68.55 ($CH_2O$), 93.66 (OCO), [127.60, 128.05, 128.32, 128.42, 129.51, 130.42, olefinic C], 173.12 (carbonyl). Some fractions containing both compounds were obtained during the chromatography and these could be recycled if necessary to give more material. The reaction scheme for this synthesis is shown in the figures below.

Example 3

Production of Monoglyceride Enriched Compositions from synthetic CGC Structured-Lipid. Model Compound for Metabolite of Compounds of the Invention.

1. 2-GLA MG (γ-linolenic acid monoglyceride) from CGC (Glycerol 1,3-didecanoate-2-γ-linolenoate)

Lipase acrylic resin from *Candida antarctica* (Sigma, Novozyme, 0.1 g,) was added to a solution of CGC (0.25 g) in ethanol (0.75 ml). The mixture was stirred at 35-40° C. and monitored by HPLC. After 3 h the resin was removed by filtration and washed with ethanol. The filtrate and washings were concentrated in vacuo. Analysis of the residual oil by HPLC indicated the formation of two major products. These were separated by chromatography on silica-boric acid. Elution with dichloromethane (DM gave an oil (fraction A, 160 mg). Further elution with DCM-MeOH (9:1) gave an oil (fraction B, 80 mg). HPLC comparison with authentic materials indicated that B was the required product i.e. 2-GLA MG (8% rearranged 1-isomer also present). The main (>90%) component of fraction A was found (by HPLC comparison and NMR) to be ethyl decanoate. The minor component was found (by HPLC and NMR) to be ethyl γ-linolenoate. These esters are expected to be formed under the reaction conditions from the corresponding acids (C and GLA) and ethanol.

Biological Studies

Example 4

Solublization of Sn-2 monoglyceride was performed using ethyl alcohol or DMSO for in vitro work on human peripheral blood mononuclear cells (PBMCs). A tendency to precipitate at acid pH may have been the cause of some animals regurgitating solid material after gavage suggesting that enterically coated formulation may be preferred. SJL mice were fed sn-2 GLA of Example 1 at three doses (50, 125 and 250 μl) for seven days by gavage. Mice receiving higher doses were prone to regurgitation. After seven days animals were killed and the brain, liver and spleen were removed the liver and brain frozen at −70° C. and mononuclear cells were isolated from spleens by sieving and density centrifugation on Lymphoprep (Sigma Chemical Co) and cultured at 37° C. in 5% CO2 atmosphere in 5 ml culture tubesat a cell density of $1\times10^6$ cells/ml in RPMI 1640 medium in 5% foetal calf serum (FCS). Cells were cultured with and without 1 µg/ml or 25 µm/ml concanavalin A (Con A) for approximately 20 hours and the supernatants removed and stored at −70° C. until required. Mouse TOP-β1 was measured in supernatants using a commercially available ELISA (Promega, Madison Wis.).

TABLE 1

Stimulated (Con A) and unstimulated TGF-β1 production pg/ml from spleen PBMCs in response to feeding of sn-2-γ-linolenoyl-glycerol monoglyceride of Example 3

| | Con A (µg/ml) | | |
|---|---|---|---|
| Monoglyceride | 0 | 1 | 25 |
| 50 µg | 377 | 409 | 480 |
| Control | 209 | 228 | 393 |
| Change % | 80 | 79 | 42 |

This shows that the metabolite of the γ-linolenoyl compound of formula of Example 2 is active in raising cytokine TGF-β1 in the same manner as Borage oil of the trial. This is consistent with modulation of all the cytokines previously shown modulated in this matter.

Example 5

In Vivo Activity of Monoglyceride Formal (Compound of Example 2)

C57/BL mice were dosed orally with 2 GLA MG formal at two doses of 50 and 150 ul for eight days. The compound was supplied in 8 separate tubes to be stored at 4° C. prior to dosing but warmed to 25° C. before use. After eight days the animals were killed and the brain, liver and spleen were removed. Liver and brain were frozen at −70° C. and mononuclear cells were isolated from spleens by sieving and density centrifugation on Lymphoprep (Sigma Chemical Co) and cultured at 37° C. in 5% $CO_2$ atmosphere in 5 ml culture tubes at a cell density of $2\times10^6$ cells/ml in RPMI 1640 medium in 5% fetal calf serum (FCS). Cells were cultured with and without 1 µg/ml or 25 µg/ml concanavalin A (Con A) for approximately 20 hrs and the supernatants removed and stored at −70° C. until required. Mouse TGF-β1 was measured in supernatants using a commercially available ELISA system (Pomega, Madison, Wis.).
Results:
Concanavalin A did not significantly stimulate TGF-β1 production in this study. Data were therefore combined for the purposes of statistical analysis (n=9/group). Data were analysed using Graphpad Instat.

TABLE 2

Spleen mononuclear cell TGFβ production (pg/ml)

| Controls | 77.9 ± 4.1 | |
|---|---|---|
| GLA 2-MG-F 50 ul | 90.9 ± 5.2 | P = 0.0702 |
| GLA 2-MG-F 150 ul | 158.6 ± 7.5 | P < 0.0001 ↑ 103% |

[Data analysed using impaired t-test; data are mean ± SEM]

REFERENCES

Amor S, Groome N, Linington C, Morris M M, Dornmair K, Gardinier M V, Matthieu J M, Baker D. Identification of epitopes of myelin oligodendrocyte glycoprotein for the induction of experimental allergic encephalomyelitis in SJL and Biozzi AB/H mice. J. Immunol. 1994 Nov. 15; 153(10):4349-56.

Beck J, Rondot P, Catinot L et al. Increased production of interferon gamma and tumor necrosis factor precedes clinical manifestation in multiple sclerosis: do cytokines trigger off exacerbations? Acta Neurol Scand 1988; 78:318-23.

Bertolotto A, Capobianco M, Malucchi S et al. Transforming growth factor beta1 (TGEbeta1) mRNA level correlates with magnetic resonance imaging disease activity in multiple sclerosis patients. Neurosci Lett 1999; 263:21-4.

Bertolotto A, Malucchi S, Capobianco M et al. Quantitative PCR reveals increased levels of tumor necrosis factor-alpha mRNA in peripheral blood mononuclear cells of multiple sclerosis patients during relapses. J Interferon Cytokine Res 1999; 19:575-81.

Brosnan C F., Selmaj K and Raine C S. Hypothesis: a role for tumor necrosis factor in immune-mediated demyelination and its relevance to multiple sclerosis. *J Neuroimmunol* 1988:18, 87-94.

Brosnan C F and Raine C S. Mechanisms of immune injury in multiple sclerosis. Brain Pathol. 1996:6, 243-257.

Burns J, Bartholomew B, Lobo S. Isolation of myelin basic protein-specific T cells predominantly from the memory T-cell compartment in multiple sclerosis. Ann Neurol 1999; 45:33-9.

Cannella B, Raine C S. The adhesion molecule and cytokine profile of multiple sclerosis lesions. Ann Neurol 1995; 37:424-35.

Chou Y K, Bourdette D N, Offner H et al. Frequency of T cells specific for myelin basic protein and myelin proteolipid protein in blood and cerebrospinal fluid in multiple sclerosis. J. Neuroimmunol 1992; 38:105-14.

De Stefano N., Narayanan S., Francis G S., Arnaoutelis R., Tartaglia M C., Antel J P., matthews P M and Arnold D L. Evidence of axonal damage in the early stages of multiple sclerosis and its relevance to disability. *Arch Neurol.* 2001: 58(1), 65-70.

Ewing C, Bernard C C. Insights into the aetiology and pathogenesis of multiple sclerosis. Immunol Cell Biol 1998; 76:47-54.

Fazakerly J K. Molecular biology of multiple sclerosis. Wiley and Sons Ltd. 1997, 255-273.

Fredrikson S, Soderstrom M, Hillert J et al. Multiple sclerosis: occurrence of myelin basic protein peptide-reactive T cells in healthy family members. Acta Neurol Scand 1994; 89:184-9.

Genain C P., Cannella B., hauser S L and Raine C S. Identification of autoantibodies associated with myelin damage in multiple sclerosis. *Nature Med* 1999:5, 170-175.

Gross C E, Bednar M M, Howard D B and Spom M B (1993) Transforming growth factor beta I reduces infarct size after experimental cerebral ischemia in a rabbit model. *Stroke* 24, 558-562.

Harbige, L S, Crawford M A, Jones J, Preece A W and Forti A. Dietary intervention studies on the phosphoglyceride fatty acids and electrophoretic mobility of erythrocytes in multiple sclerosis. *Prog. Lipid Res* 1986:25, 243-248.

Harbige L S. Nutrition and immunity with emphasis on infection and autoimmune disease. (1996) *Nutr Health,* 10(4): 285-312.

Harbige L S (1998) Dietary n-6 and n-3 fatty acids in immunity and autoimmune disease. *Proceedings of the Nutrition Society* 57, 555-562.

Harbige L S, Yeatman N, Amor S & Crawford M A (1995) Prevention of experimental autoimmune encephalomyelitis in Lewis rats by a novel source of γ-linolenic acid. *British Journal of Nutrition* 74, 701-715.

Harbige L S., Layward L., Morris-Downes M M., Dumonde D C and Amor S. The protective effects of omega-6 fatty acids in experimental autoimmune encephalomyelitis (EAE) in relation to transforming growth factor-beta 1 (TGF-beta1) up-regulation and increased prostaglandin E2 (PGE2) production. *Clin Exp Immunol* 2000:122, 445-452.

Henrich Noack P, Prehn J H, and Kriegistein J. (1996) TGF-beta I protects hippocampal neurons against degeneration caused by transient global ischaemia. Dose-response relationship and potential neuroprotective mechanisms. *Stroke,* 27, 1609-1614.

Hirsch R L, Panitch H S, Johnson K P. Lymphocytes from multiple sclerosis patients produce elevated levels of gamma interferon in vitro. J Clin Immunol 1985; 5:386-9.

Hollifield R D, Harbige L S, PhM-Dinh D, Sharief M. Evidence for cytokine Dysregulation in Multiple Sclerosis: Peripheral Blood Mononuclear cell production of pro-inflammmatory and anti-inflammatory cytokines during relapse and remission. *Autoimmunity,* 2003 36(3): 133-141.

Imamura K, Suzumura A, Hayashi F et al. Cytokine production by peripheral blood monocytes/macrophages in multiple sclerosis patients. Acta Neurol Scand 1993; 87:281-5.

Issazadeh S, Lorentzen J C, Mustafa M I et al. Cytokines in relapsing experimental autoimmune encephalomyelitis in DA rats: persistent mRNA expression of proinflammatory cytokines and absent expression of interleukin-10 and transforming growth factor-beta. J Neuroimmunol 1996; 69:103-15.

Johns L D, Sriram S. Experimental allergic encephalomyelitis: neutralizing antibody to TGF beta 1 enhances the clinical severity of the disease. J Neuroimmunol 1993; 47:1-7.

Kerlero de Rosbo N, Hoffman M, Mendel I et al. Predominance of the autoimmune response to myelin oligodendrocyte glycoprotein (MOG) in multiple sclerosis: reactivity to the extracellular domain of MOG is directed against three main regions. Eur J Immunol 1997; 27:3059-69.

Kerlero de Rosbo N, Milo R, Lees M B et al. Reactivity to myelin antigens in multiple sclerosis. Peripheral blood lymphocytes respond predominantly to myelin oligodendrocyte glycoprotein. J Clin Invest 1993; 92:2602-8.

Khalil N. TGF-beta: from latent to active. Microbes Infect 1999; 1:1255-63.

Krupinski J, Kumar P, Kumar S, and Kaluza J. (1996) Increased expression of TGF-beta I in brain tissue after ischemic stroke in humans. *Stroke,* 27, 852-857.

Kuroda Y, Shimamoto Y. Human tumor necrosis factor-alpha augments experimental allergic encephalomyelitis in rats. J Neuroimmunol 1991; 34:159-64.

Lu C Z, Jensen M A, Amason B G. Interferon gamma- and interleukin-4-secreting cells in multiple sclerosis. J Neuroimmunol 1993; 46:123-8.

Maimone D, Reder A T, Gregory S. T cell lymphokine-induced secretion of cytokines by monocytes from patients with multiple sclerosis. Cell Immunol 1993; 146:96-106.

Martino G, Hartung H-P. Immunopathogenesis of multiple sclerosis: the role of T cells. Curr Opin Neurol 1999; 12:309-21.

McCarron R M, Wang L, Racke M K et al. Cytokine-regulated adhesion between encephalitogenic T lymphocytes and cerebrovascular endothelial cells. J Neuroimmunol 1993; 43:23-30.

McDonald W I, Compston A, Edan G, Goodkin D, Hartung H P, Lublin F D, McFarland H F, Paty D W, Polman C H, Reingold S C, Sandberg-Wollheim M, Sibley W, Thompson A, van den Noort S, Weinshenker B Y, Wolinsky J S. Recommended diagnostic criteria for multiple sclerosis: guidelines from the International Panel on the diagnosis of multiple sclerosis. Ann Neurol. 2001 July; 50(1):121-7.

Merrill J E, Strom S R, Ellison G W et al. In vitro study of mediators of inflammation in multiple sclerosis. J Clin Immunol 1989; 9:84-96.

Merrill J E, Zimmerman R P. Natural and induced cytotoxicity of oligodendrocytes by microglia is inhibitable by TGF beta. Glia 1991; 4:327-31.

Miyazono K, Hellman U, Wernstedt C et al. Latent high molecular weight complex of transforming growth factor beta 1. Purification from human platelets and structural characterization. J Biol Chem 1988; 263:6407-15.

Mokhtarian F, Shi Y, Shirazian D et al. Defective production of anti-inflammatory cytokine, TGF-beta by T cell lines of patients with active multiple sclerosis. J Immunol 1994; 152:6003-10.

Navikas V, Link H. Review: cytokines and the pathogenesis of multiple sclerosis. J Neurosci Res 1996; 45:322-33.

Noseworthy J H. Progress in determining the causes and treatment of multiple sclerosis. Nature 1999:399(6738 Suppl), A40-47.

Ota K, Matsui M, Milford E L et al. T-cell recognition of an immunodominant myelin basic protein epitope in multiple sclerosis. Nature 1990; 346:183-7.

Perkin G D, Wolinsky J S. Fast facts-Multiple Sclerosis, 1st Edn. Oxford, UK: Health Press, 2000.

Philippe J, Debruyne J, Leroux-Roels G et al. In vitro TNF-alpha, IL-2 and IFN-gamma production as markers of relapses in multiple sclerosis. Clin Neurol Neurosurg 1996; 98:286-90.

Phylactos A C, Ghebremeskel K, Costeloe K, Leaf A A, Harbige L S, Crawford M A. (1994) Polyunsaturated fatty acids and antioxidants in early development. Possible prevention of oxygen-induced disorders. Eur J Clin Nutr. 48Suppl 2:S17-23.

Prehn J H, Peruche B, Unsicker K and Kriegistein J. (1993) Isoform-specific effects of transforming growth factor-beta on degeneration of primary neuronal cultures induced by cytotoxic hypoxia or glutamate. *J. Neurochem.* 60, 1665-1672.

Rack M K, Sriram S, Calrimi J, Cannella B, Raine C S & McFarim D E (1993) Long-term treatment of chronic relapsing experimental allergic encephalomyelitis by transforming growth factor-p2. *Journal of Neuroimmunology,* 46, 175-183.

Racke M K, Cannella B, Albert P et al., Evidence of endogenous regulatory function of transforming growth factor-beta 1 in experimental allergic encephalomyelitis. Int Immunol 1992; 4:615-20.

Rieckmann P, Albrecht M, Kitze B et al. Cytokine mRNA levels in mononuclear blood cells from patients with multiple sclerosis. Neurology 1994; 44:1523-6.

Rieckmann P, Albrecht M, Kitze B et al. Tumor necrosis factor-alpha messenger RNA expression in patients with relapsing-remitting multiple sclerosis is associated with disease activity. Ann Neurol 1995; 37:82-8.

Ruddle N H, Bergman C M, McGrath K M et al. An antibody to lymphotoxin and tumor necrosis factor prevents transfer of experimental allergic encephalomyelitis. J Exp Med 1990; 172:1193-200.

Santambrogio L, Hochwald G M, Saxena B, Leu C H, Martz J E, Carlin J A, Ruddle N H, Palladino M A, Gold L I & Thorbecke G J (1993) Studies on the mechanisms by which Transforming Growth Factor-p protects against allergic encephalomyelitis. *Journal of Immunology* 151, 1116-1127.

Schiefer H B, Hancock D S, Loew F M. Long-term effects of partially hydrogenated herring oil on the rat myocardium. Drug Nutr Interact. 1982; 1(2):89-102.

Schluesener H J, Lider O. Transforming growth factors beta 1 and beta 2: cytokines with identical immunosuppressive effects and a potential role in the regulation of autoimmune T cell function. J Neuroimmunol 1989; 24:249-58.

Selmaj K, Raine C S, Cannella B et al. Identification of lymphotoxin and tumor necrosis factor in multiple sclerosis lesions. J Clin Invest 1991; 87:949-54.

Selmaj K., Raine C S, Farooq M et al. Cytokine cytotoxicity against oligodendrocytes. Apoptosis induced by lymphotoxin. J Immunol 1991; 147:1522-9.

Sharief M K, Thompson E J. In vivo relationship of tumor necrosis factor-alpha to blood-brain barrier damage in patients with active multiple sclerosis. J Neuroimmunol 1992; 38:27-33.

Tejada-Simon M V, Hong J, Rivera V M et al. Reactivity pattern and cytokine profile of T cells primed by myelin peptides in multiple sclerosis and healthy individuals. Eur J Immunol 2001; 31:907-17.

Vartanian T, Li Y, Zhao M et al., Interferon-gamma-induced oligodendrocyte cell death: implications for the pathogenesis of multiple sclerosis. Mol Med 1995; 1:732-43.

Vivien D, Bemaudin M, Buisson A, Divoux D, MacKenzie E T and Nouvelot A. (1998) Evidence of type I and type PI transforming growth factor-beta receptors in central nervous tissues: changes induced by focal cerebral ischemia. *J. Neurochem.* 70, 2296-2304.

Zhang J, Markovic-Plese S, Lacet B et al. Increased frequency of interleukin 2-responsive T cells specific for myelin basic protein and proteolipid protein in peripheral blood and cerebrospinal fluid of patients with multiple sclerosis. J Exp Med 1994; 179:973-84.

Japanese Patent 6172263 (1994) Y. Kosugi et al, Agency of Industrial Science & Technology High-purity arachidonic acid triglyceride and its production.

U.S. Pat. No. 4,888,324 (1989) N. Catsimpoolas et al, Angio-Medical Corporation Method for enhancing angiogenesis with lipid containing molecules.

Y. Kosugi and N. Azuma, *J Amer. Oil Chem. Soc.*, 71, 1397-1403 (1994). Synthesis of Triacylglycerol from polyunsaturated fatty acid by immobilized ipase.

J. W. Hageman et al, J. Amer, Oil Chem. Soc., 49, 118-xxx (1972) Preparation of Glycerin and their Uses.

E. S. Lutton and A. J. Fehl, Lipids, 5, 90-99 (1970). The polymorphism of odd and even saturated single acid triglycerides, $C_8$-$C_{22}$.

D. Horrobin, A. McMordie, M. S. Manku (Scotia Holdings PLC UK) Eur. Pat. Appl EP 609078 3 Aug. 1994. Phospholipids containing two different unsaturated fatty acids for use in therapy, nutrition, and cosmetics.

Y.-S. Huang, X. Lin, P. R. Redden and D. F. Horrobin, *J. Am. Oil Chem. Soc.*, 72, 625-631, (1995). In vitro Hydrolysis of Natural and Synthetic γ-Linolenic Acid-Containing Triacylglycerols by Pancreatic Lipase K. Osada, K. Takahashi, M. Hatano and M. Hosokawa, *Nippon Suisan Gakkaishi.*, 57, 119-125 (1991). Chem. Abstr., 115:278299 Molecular Species of Enzymically-synthesized Polyunsaturated Fatty acid-rich Triglycerides.

J.-W. Liu, S. DeMichele, M. Bergana, E. Bobik, Jr., C. Hastilow, Lu-Te Chuang, P. Mukerji and J.-S. Huang., *J. Am. Oil Chem. Soc.*, 78, 489-493 (2001) Characterization of Oil Exhibiting High γ-Linolenic Acid from a Genetically transformed Canola Strain.

D. R. Kodali, D. Atkinson, T. G. Redgrave and D. Small, *J. Lipid Res.*, 28, 403-413 (1987). Structure and polymorphism of 18-Carbon Fatty Acid Triacylglycerols: Effect of Unsaturation and Substitution in the 2-Position P. H. Bentley and W. McCrae, *J. Org. Chem.* 35, 2082-2083 (1970) An Efficient Synthesis of Symmetrical 1,3-Diglycerides.

M. Berger, K. Laumen and M. P. Schneider, *J. Am. Oil. Chem. Soc.*, 69, 955-959, (1992). Enzymatic Esterification of Glycerol 1. Lipase-Catalyzed Synthesis of Regioisomerically Pure 1,3-sn-Diacylglycerols.

A. P. J. Mank, J. P. Ward and D. A. van Dorp, *Chem. Physics Lipids*, 16, 107-114 (1976). A versatile, flexible synthesis of 1,3-diglycerides and triglycerides.

L. Hartman, *Chem. Rev.*, 58, 845-867 (1958) and references therein. Advances in the Synthesis of Glycerides of Fatty Acids

The invention claimed is:

1. A method of treating a patient in need of cytokine modulation comprising administering to that patient a therapeutically effective dose of a glyceride or compound of general formula I

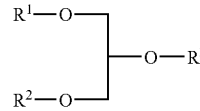

wherein $R^1$ and $R^2$ together form a group —$(CH_2)_n$—$CR^4R^5$—$(CH_2)_m$— wherein n and m are independently selected integers 0, 1 or 2 and $R^4$ and $R^5$ are independently selected from H, $C_{1-18}$ alkyl, $C_{1-18}$ alkoxy, $C_{1-18}$ hydroxyalkyl, $C_{2-18}$ alkenyl and $C_{6-18}$ aryl or aralkyl and $R^3$ is a fatty acyl group of an essential polyunsaturated fatty acid selected from the group consisting of γ-linolenoyl and γ-dihomolinolenoyl.

2. A method as claimed in claim 1 wherein $R^1$ and $R^2$ form a group —$CR^4R^5$— wherein $R^4$ and $R^5$ are independently selected from H and $C_{1-6}$ alkyl.

3. A method as claimed in claim 1 wherein $R^1$ and $R^2$ form a group —$CH_2$— or —$CH_2CH_2$—.

4. A method as claimed in claim 1 wherein the compound of claim 1 is an n3-fatty acyloxy-1,3-dioaxan or an n-6 fatty acyloxy-1,3-dioxan.

5. A method as claimed in claim 1 wherein the compound of formula I is selected from a the group consisting of 5-γ-linolenoyloxy-1,3-dioxans and 5-dihomo-γ-linolenoyloxy-1,3-dioxan.

6. A method as claimed in claim 1 wherein the patient is in need of therapy for cytokine dysregulation.

7. A method as claimed in claim 1 wherein the patient is in need of therapy to prevent demyelination in a neurodegenerative disease.

8. A method as claimed in claim 1 wherein the modulated cytokines are one or more of TGF-β1, TNF-α, IL-β1, IL4, IL5, IL6, IL8, IL10, IL13, and γ-IFN.

9. A method as claimed in claim 1 wherein the treatment is for abnormalities of the immune system.

10. A method as claimed in claim 9 wherein the treatment is for a condition selected from the group consisting of systemic lupus erythematosus (SLE), allergy, asthma, Crohn's disease and rheumatoid arthritis, multiple sclerosis, neurodegenerative diseases sequelae of stroke, head trauma, bleeds and the chronic abnormalities of Alzheimer's and Parkinson's disease, coronary heart disease (CHD) abnormalities of pre-mature infants and sepsis.

11. A compound of formula I

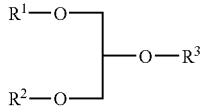

wherein $R^1$ and $R^2$ together form a group —$(CH_2)_n$—$CR^4R^5$—$(CH_2)_m$— wherein n and m are independently selected integers 0, 1 or 2 and $R^4$ and $R^5$ are independently selected from H, $C_{1-18}$ alkyl, $C_{1-18}$ alkoxy, $C_{1-18}$ hydroxyalkyl, $C_{2-18}$ alkenyl and $C_{6-18}$ aralkyl
and $R^3$ selected from the group consisting of γ-linolenoyl and γ-dihomolinolenoyl.

12. A compound as claimed in claim 11 wherein $R^1$ and $R^2$ form a group —$CR^4R^5$ where $R^4$ and $R^5$ are independently selected from H and $C_{1-6}$ alkyl.

13. A compound as claimed in claim 11, wherein $R^1$ and $R^2$ form a group —$CH_2$— or —$CH_2CH_2$—.

14. A compound as claimed in claim 11 being a 5-acyloxy-1,3-dioxan.

15. A compound as claimed in claim 11 being an n-6 fatty acyloxy-1,3-dioxan.

16. A compound as claimed in claim 11 being selected from the group consisting of a 5-γ-linolenyloxy-1,3-dioxan and a 5-dihomo-γ-linolenyloxy-1,3-dioxan.

17. A composition for use in the method of the present invention comprising a compound of formula I as claimed in claim 11 together with a pharmaceutically or nutraceutically acceptable carrier, coating, capsule, diluent and/or preservative.

18. A composition as claimed in claim 17 comprising a preservative which is an antioxidant or inhibitor of transesterification.

19. A composition as claimed in claim 18 comprising 0.05 mg/g or less of Vitamin E.

20. A pharmaceutical composition for regulating the immune system comprising a compound of general formula I as defined in claim 1.

21. A method as claimed in claim 1 wherein the neurodegenerative disease involves demyelination.

22. A method as claimed in claim 1 wherein the treatment specifically arrests underlying neurodegeneration and restores neuronal function.

23. A method as claimed in claim 1 which normalises neuronal membrane composition with respect to γ-linolenic acid, dihomo-γ-linolenic acid and arachidonic acid lipid content.

24. A method as claimed in claim 1 which restores healthy TGF-β1/TNFα ratios as measured from spontaneous release from peripheral blood mononuclear cell release.

25. A method as claimed in claim 1 wherein the disease is relapsing remitting multiple sclerosis, primary progressive multiple sclerosis or chronic progressive multiple sclerosis.

26. A method as claimed in claim 1 wherein the treatment is of cerebral impairment after stroke, head trauma and intracranial bleeding, Alzheimer's disease or Parkinson's disease where there is demyelination or neuronal damage.

27. A method as claimed in claim 1 wherein the lipid is administered for a duration and at a dose sufficient to maintain or elevate TGF-β1 levels in the patient to therapeutic levels.

28. A method as claimed in claim 1 wherein the lipid is administered for a duration and at a dose sufficient to maintain or elevate TGF-β1 levels in the patient to a TGF-β1/TNF-α ratio released spontaneously from peripheral blood mononuclear cells isolated from the blood of a patient, after 18 months of daily dosing, of 0.4 to 3.0, at least 0.5, more preferably at least 0.75 and most preferably at least 1.

29. A method as claimed in claim 1 wherein the dose is such as to produce a TGF-β1/IL-1β ratio in PBMCs isolated from blood of a patient, after 18 months of daily dosing, of at least of at least 0.75.

30. A method as claimed in claim 1 wherein the amount of compound administered is between 0.5 and 30 grams, typically 3 to 5 grams, per day.

31. A method, use or composition as claimed in claim 1 wherein $R^3$ is γ-linolenyl or dihomo-γ-linolenyl and the dose is between 1 and 10 grams/day.

32. A method, use or composition as claimed in claim 31 wherein the dose is between 2 and 10 grams/day.

* * * * *